US012631605B2

(12) United States Patent
Mason et al.

(10) Patent No.: US 12,631,605 B2
(45) Date of Patent: May 19, 2026

(54) ACOUSTIC MIST IONISATION AND NEWBORN DRIED BLOOD SPOT SCREENING

(71) Applicant: Micromass UK Limited, Wilmslow (GB)

(72) Inventors: Donald Mason, Haverhill, MA (US); Heather Brown, Stockport (GB)

(73) Assignee: Micromass UK Limited, Wilmslow (GB)

( * ) Notice: Subject to any disclaimer, the term of this patent is extended or adjusted under 35 U.S.C. 154(b) by 851 days.

(21) Appl. No.: 17/599,286

(22) PCT Filed: Mar. 30, 2020

(86) PCT No.: PCT/GB2020/050844
§ 371 (c)(1),
(2) Date: Sep. 28, 2021

(87) PCT Pub. No.: WO2020/201734
PCT Pub. Date: Oct. 8, 2020

(65) Prior Publication Data
US 2022/0170895 A1      Jun. 2, 2022

Related U.S. Application Data

(60) Provisional application No. 62/826,329, filed on Mar. 29, 2019.

(51) Int. Cl.
*G01N 30/88*          (2006.01)
*A61B 5/01*           (2006.01)
(Continued)

(52) U.S. Cl.
CPC .............. *G01N 30/88* (2013.01); *A61B 5/01* (2013.01); *B05B 17/0615* (2013.01);
(Continued)

(58) Field of Classification Search
CPC .. G01N 30/88; G01N 2030/8822; A61B 5/01; A61B 2503/045; B05B 17/0615; C12Q 1/6883; H01J 49/0454
See application file for complete search history.

(56) References Cited

U.S. PATENT DOCUMENTS

2002/0109084 A1*   8/2002   Ellson ................. H01J 49/0454
                                                             250/288
2007/0131871 A1    6/2007   Chang et al.
(Continued)

FOREIGN PATENT DOCUMENTS

DE        10 2016 125204 A1      6/2017

OTHER PUBLICATIONS

International Search Report and Written Opinion for International Application No. PCT/GB2020/050844, mailed Jun. 15, 2020.
(Continued)

*Primary Examiner* — Rebecca M Fritchman
(74) *Attorney, Agent, or Firm* — Goodwin Procter LLP

(57) ABSTRACT
A method of newborn screening ("NBS") is disclosed comprising directing ultrasonic energy or ultrasonic waves into a metabolite or analyte sample derived from a newborn, neonate or infant so as to cause a mist of charged sample droplets or sample ions to be ejected. The charged sample droplets or sample ions are then mass analysed and a determination is made as to whether or not one or more first metabolites or analytes indicative of a disorder or inborn error are present in the sample.

16 Claims, 6 Drawing Sheets

(51) Int. Cl.
    B05B 17/06         (2006.01)
    C12Q 1/6883      (2018.01)
    H01J 49/04       (2006.01)

(52) U.S. Cl.
    CPC ........ C12Q 1/6883 (2013.01); H01J 49/0454
          (2013.01); *A61B 2503/045* (2013.01); *G01N*
                             *2030/8822* (2013.01)

(56)                References Cited

U.S. PATENT DOCUMENTS

| | | | |
|---|---|---|---|
| 2012/0080592 A1* | 4/2012 | Wiseman ............ | H01J 49/0459 |
| | | | 250/288 |
| 2014/0283628 A1* | 9/2014 | Hattingh ............. | H01J 49/0454 |
| | | | 73/864.81 |
| 2016/0281166 A1* | 9/2016 | Bhattacharjee ........ | G16B 35/00 |

OTHER PUBLICATIONS

Edwards, R.L., et al., "Top-Down Proteomics and Direct Surface Sampling of Neonatal Dried Blood Spots: Diagnosis of Unknown Hemoglobin Variants", Journal of the American Society for Mass Spectrometry, 23(11):1921-1930, Sep. 20, 2012.

Chace, D.H., et al., "Use of Tandem Mass Spectrometry for Multianalyte Screening of Dried Blood Specimens From Newborns", Clinical Chemistry, P.B. Hoeber, 49(11):1797-1817, Jan. 1, 2003.

Chen-I Wu, et al., "Ultrasound Ionization of Biomolecules", Rapid Communications in Mass Spectrometry, 24(17):2569-2574, Sep. 15, 2010.

Giancarlo la Marca, "Mass Dpectrometry in Clinical Chemistry: the Case of Newborn Screening", Journal of Pharmaceutical and Biomedical Analysis, p. 1-9, (2014).

\* cited by examiner

To MS Detector

6

7 Mass Spec Front-end
Waters Xevo G2-XS QTof

Heated Transfer Interface
150-400°C

Collection Nozzle
applies electric field 384-well Microtitre Plate
Echo® Qualified

4

Acoustic Transducer Assembly
modified Echo® 555

3

NBS Workflow (In-plate ISTDs/AMI)

31 → Punch 3mm DBS into 96-well pre-coated microtitre plate

32 → Add 100µL extraction solvent-cover plate

33 → Shake for 30 minutes at 37°C

34 → Transfer extract to acoustic plate

35 → Load onto AMI-MS/MS

ACOUSTIC MIST IONISATION AND NEWBORN DRIED BLOOD SPOT SCREENING

CROSS-REFERENCE TO RELATED APPLICATIONS

This application is a U.S. national phase filing claiming the benefit of and priority to International Patent Application No. PCT/GB2020/050844, filed Mar. 30, 2020, which claims priority from and the benefit of U.S. Provisional Application No. 62/826,329 filed on Mar. 29, 2019. The entire contents of these applications are incorporated herein by reference.

FIELD OF THE INVENTION

The present invention relates generally to mass spectrometers and methods of mass spectrometry. Various embodiments are disclosed which relate to an improved method of newborn screening ("NBS") of dried blood spots ("DBS") utilising an acoustic mist ionisation ion source.

BACKGROUND

Newborn screening ("NBS") for inborn errors of metabolism began in the early 1960s with the development by Dr Robert Guthrie of the "Guthrie Test" for screening a presumptively healthy newborn population for the disorder of phenylalanine metabolism, phenylketonuria ("PKU"). This simple bacterial inhibition assay possessed a number of desirable attributes that allowed its use for population-wide screening. It was inexpensive, simple to perform, could detect disease pre-symptomatically and could be performed on a dried blood sample that was minimally invasive to collect from a newborn 24-48 hours post-partum.

These attributes have remained the hallmarks of subsequent newborn screening tests that have been developed in the intercalating six decades.

One limitation of the Guthrie Test for phenylketonuria was the need to develop separate screening tests for other newborn disorders which were desired to be screened for at the same time. In particular, each additional screening test required a separate dried blood spot to be obtained and it will be readily apparent that it can be rather onerous to obtain multiple dried blood spots from a newborn child.

When newborn screening labs began offering tests for congenital hypothyroidism (mid-1970s), galactosemia (mid-1980s) and sickle cell disease (late 1980s) the number of dried blood spots which were required from a newborn increased yet further and the number of analytical testing platforms also increased.

It was not until the introduction of Electrospray Ionization ("ESI") coupled with tandem mass spectrometry in the late 1990s that high throughput multi-analyte newborn screening became possible utilising a single punch (typically 3 mm) taken from a dried blood spot on a card.

Today, more than 30 inborn metabolic disorders can be screened for in a single analysis. Sample from a single dried blood spot is extracted and then subjected to flow-injection analysis utilising a tandem mass spectrometer ("FIA-MS/MS").

A typical known analytical platform for screening for inborn metabolic disorders comprises utilising a solvent delivery pump and an automated sample handler. The automated sample handler is capable of transferring a small volume (typically 5-20 µL) of extract taken from a dried blood spot into a solvent flow path.

The solvent and sample metabolites dissolved therein, are then introduced into the ion source of the mass spectrometer and disease-specific ions are measured and reported.

The entire process, from injection of one newborn sample to the next is relatively slow, requiring approximately 2 minutes, and can be prone to contamination or carry-over effects from one sample to the next, particularly in cases of elevated metabolite concentrations as will typically be present in the case of a newborn with a metabolic disorder.

The use of a solvent pump and auto-sampler also introduces complexity into the analytical workflow.

The solvent delivery and injection systems have numerous moving parts and hence can be prone to frequent failures which necessitate regular preventative and corrective maintenance.

It is therefore desired to provide an improved method of screening and in particular to provide an improved method of newborn screening ("NBS").

SUMMARY

According to an aspect there is provided a method of newborn screening ("NBS") comprising:

directing ultrasonic energy or ultrasonic waves into a metabolite or analyte sample derived from a newborn, neonate or infant so as to cause a mist of charged sample droplets or sample ions to be ejected;

mass analysing the charged sample droplets or sample ions; and determining whether or not one or more first metabolites or analytes indicative of a disorder or inborn error are present in the sample.

The disorder may be a metabolite or metabolic disorder. Other embodiments are contemplated wherein a determination may be made as to whether or not there is an inborn error such as an inborn error of endocrinology or hematology.

Various embodiments relate to the use of Acoustic Mist Ionisation ("AMI") which is also known as Acoustic Droplet Ejection ("ADE") to ionise a metabolite sample which has been obtained from a newborn, neonate or infant. The use of an Acoustic Mist Ionisation ion source has been found to be particularly beneficial when seeking to analyse a newborn, neonate or infant sample. The approach according to various embodiments overcomes limitations which are inherent with using a conventional sample delivery system as discussed above.

Furthermore, the conventional approach to newborn screening utilises analytical instruments which use a relatively complex Liquid Chromatography pump.

The present inventors have recognised that newborn screening can be simplified and the process sped up by utilising an Acoustic Mist Ionisation ion source to ionise metabolite samples thereby rendering a solvent delivery system redundant.

Acoustic Mist Ionisation uses acoustic energy or acoustic waves to transfer and ionise liquid samples without making physical contact with the samples. A burst of acoustic energy or acoustic waves is applied beneath the well of a sample wellplate (typically comprising 96 or 384 sample wells) and wherein a sample to be analysed has been dispensed into at least some of the sample wells. The burst of acoustic energy or acoustic waves causes a small volume of the liquid or solvent contained within the sample well of the sample plate to be ejected.

A collection electrode or nozzle is arranged above the sample well or sample plate and a relatively high voltage is applied to the collection electrode. As a result, charge separation effects occur within the liquid sample. Furthermore, the burst of acoustic energy or acoustic waves results in a fine mist of charged droplets being ejected from the upper surface of the sample well. Accordingly, a portion of the sample in the sample well is ionised and charged droplets are ejected which are attracted or otherwise drawn towards the collection electrode.

The charged sample droplets which are ejected from the sample well are then transferred through a heated transfer interface and are passed to the input stage of a mass spectrometer. The charged sample or analyte ions are then analysed by the mass spectrometer and mass spectral data is obtained. Analyte and internal standard ions can then be detected and measured and a ratio of the ion intensity of the analyte to that of the internal standard can be calculated, allowing a determination to be made as to whether or not the metabolites are present in the sample at a concentration which may be indicative of a disorder. In particular, the one or more metabolites may be indicative of a metabolic disorder with the newborn, neonate or infant or an inborn-error of metabolism. Other embodiments are also contemplated wherein the metabolites may be indicative of inborn-errors of endocrinology or hematology.

More generally, the method disclosed herein is also applicable for screening for inborn errors such as inborn errors of endocrinology or hematology.

The method may comprise preparing the metabolite sample for analysis by punching, clipping or removing a portion of a dried blood spot ("DBS") relating to a newborn, neonate or infant (or child or adult) and transferring the portion into a sample well of a first sample plate.

The first sample plate may comprise a microtitre plate. For example, the first sample plate may comprise a 96-well microtitre plate.

The method may further comprise adding an extraction sample or solvent to the dried blood spot portion in the sample well of the first sample plate.

The extraction sample or solvent may have the effect of drawing out metabolites or other analytes of interest from the dried blood sample so that the metabolites or other analytes become dissolved in the solvent.

The method may further comprise shaking or agitating the dried blood spot portion and extraction sample or solvent in the sample well of the first sample plate.

The process of shaking or agitating the sample may further enhance the transfer of metabolites into the solvent solution.

The method may further comprise transferring an extract from the sample well of the first sample plate into a sample well of a second sample plate.

The second sample plate may comprise a microtitre plate. For example, the second sample plate may comprise a 96-well or 384-well microtitre plate. If the first sample plate comprises a 96-well microtitre or other sample plate then the second sample plate may also comprise a similarly formatted 96-well microtitre or other sample plate. The second sample plate may comprise an acoustic sample plate or an acoustic microtitre plate which is acoustically transparent so as to facilitate the transfer of acoustic energy through the base of the sample plate and into the liquid sample.

The method may further comprise loading or positioning the second sample plate for analysis and/or ionisation between an acoustic transducer assembly and a collection nozzle or electrode.

Accordingly, the second sample plate which may comprise an acoustic sample plate may be loaded into position and in a manner wherein the acoustic transducer assembly does not contact the sample within a sample well of the sample plate.

The step of directing ultrasonic energy or ultrasonic waves into the metabolite sample may comprise energising the acoustic transducer assembly.

According to various embodiments, the acoustic transducer assembly may be pulsed ON or otherwise energised in order to transmit a pulse of ultrasonic waves, ultrasonic energy, acoustic waves or acoustic energy into the liquid sample contained within a sample well of a sample plate.

The step of directing ultrasonic energy or ultrasonic waves into the metabolite sample may comprise energising the acoustic transducer assembly to emit ultrasonic waves having a frequency in a range: (i) 20-30 kHz; (ii) 30-40 kHz; (iii) 40-50 kHz; (iv) 50-60 kHz; (v) 60-70 kHz; (vi) 70-80 kHz; (vii) 80-90 kHz; (viii) 90-100 kHz; or (ix) >100 kHz.

The term "ultrasonic" should be construed as relating to acoustic waves which have a frequency above the upper limit of human hearing which is approximately 20 kHz.

The method may further comprise arranging the acoustic transducer assembly so that the acoustic transducer assembly does not directly contact the metabolite sample.

A particular advantage in the context of newborn, neonate or infant screening (wherein high levels of metabolites or other analytes of interest may be present) is that the ion source which effectively includes the acoustic transducer does not come into direct physical contact with the sample to be analysed. Accordingly, potential cross contamination and carry-over problems are either substantially reduced or entirely avoided.

The method may further comprise applying an electric field between the collection nozzle or electrode and the sample well of the second sample plate in order to direct sample droplets into a transfer interface.

The application of a relatively high voltage or potential to the collection nozzle or electrode results in the generation of an electric field which both induces charge separation effects within the sample in the sample well and which also acts to accelerate charged droplets emitted from the upper surface of the sample towards the collection nozzle or electrode and onwards into the transfer interface.

The method may further comprise heating the transfer interface optionally to a temperature in the range 150-400° C., further optionally to a temperature in the range 200-300° C.

It has been found that heating the transfer interface in the temperature range 150-400° C. and further in the temperature range 200-300° C. improves the transfer of (charged) sample droplets from the collection nozzle or electrode to the initial stages of a mass spectrometer.

According to various embodiments the one or more first metabolites or other analytes of interest may comprise: (i) adenosine deaminase ("ADA"); (ii) purine nucleoside phosphorylase ("PNP"); (iii) human platelet antigens ("HPA"); (iv) metabolites indicative of a hemoglobinopathy; and (v) phenylalanine metabolites indicative of phenylketonuria ("PKU").

According to various embodiments the one or more first metabolites or analytes may comprise free carnitine, acyl-carnitines, amino acids, products of lysosomal enzymes, peptides or proteins indicative of hemoglobinopathy.

It will be understood that numerous different metabolites or analytes indicative of a disorder or inborn error may be tested for. Other metabolites and analytes other than those detailed above may be tested for according to other embodiments.

According to another aspect there is provided a method of mass spectrometry comprising a method as disclosed above.

According to another aspect there is provided a mass spectrometer comprising:

an acoustic transducer assembly arranged and adapted to direct ultrasonic energy or ultrasonic waves into a metabolite or analyte sample derived from a newborn, neonate or infant so as to cause a mist of charged sample droplets or sample ions to be ejected;

a mass analyser for mass analysing the charged sample droplets or sample ions; and a control system arranged and adapted to determine whether or not one or more first metabolites or analytes indicative of a disorder or inborn error are present in the sample, wherein the one or more first metabolites or analytes comprise free carnitine, acylcarnitines, amino acids, products of lysosomal enzymes, peptides or proteins indicative of hemoglobinopathy.

According to other embodiments the control system may be arranged and adapted to determine whether or not one or more first metabolites or analytes indicative of a disorder or inborn error are present in the sample, wherein the one or more first metabolites or analytes comprise: (i) adenosine deaminase ("ADA"); (ii) purine nucleoside phosphorylase ("PNP"); (iii) human platelet antigens ("HPA"); (iv) metabolites indicative of a hemoglobinopathy; and (v) phenylalanine metabolites indicative of phenylketonuria ("PKU").

Other embodiments are contemplated wherein the screening method may be applied to infants, children and adults. For example, according to various embodiments the method of dried blood spotting and screening may be applied to screen children and adults for PKU.

Accordingly, other embodiments relate to a method of screening comprising:

directing ultrasonic energy or ultrasonic waves into a metabolite or analyte sample derived from a patient so as to cause a mist of charged sample droplets or sample ions to be ejected;

mass analysing the charged sample droplets or sample ions; and determining whether or not one or more first metabolites or analytes indicative of a disorder or inborn error are present in the sample.

The patient may be a human newborn, neonate, infant, child or adult.

BRIEF DESCRIPTION OF THE DRAWINGS

Various embodiments will now be described, by way of example only, and with reference to the accompanying drawings in which.

6

Figure 3:
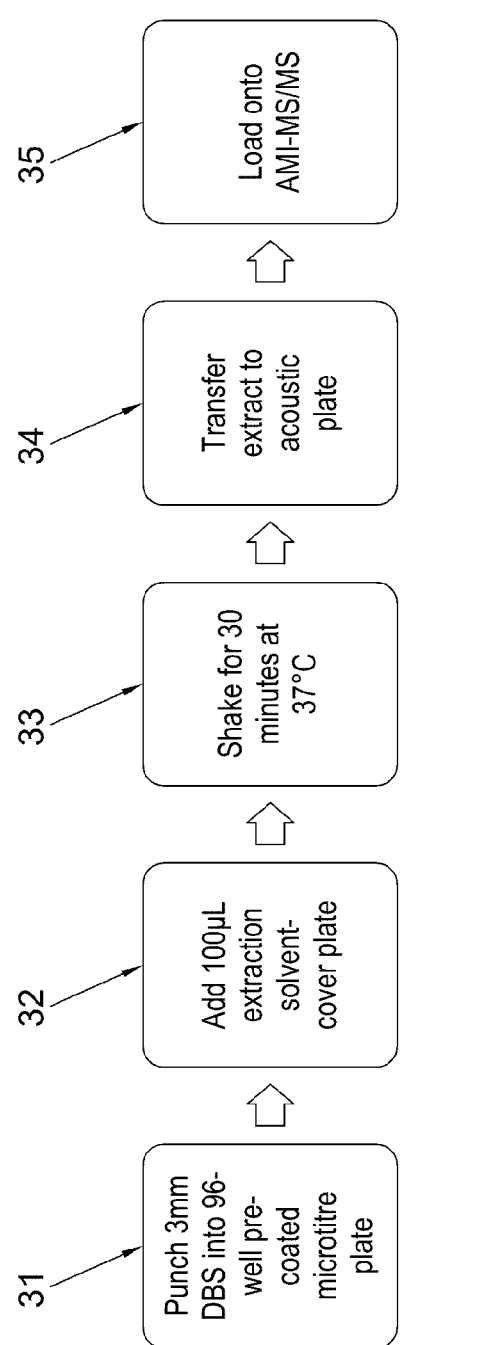
Figure 4:
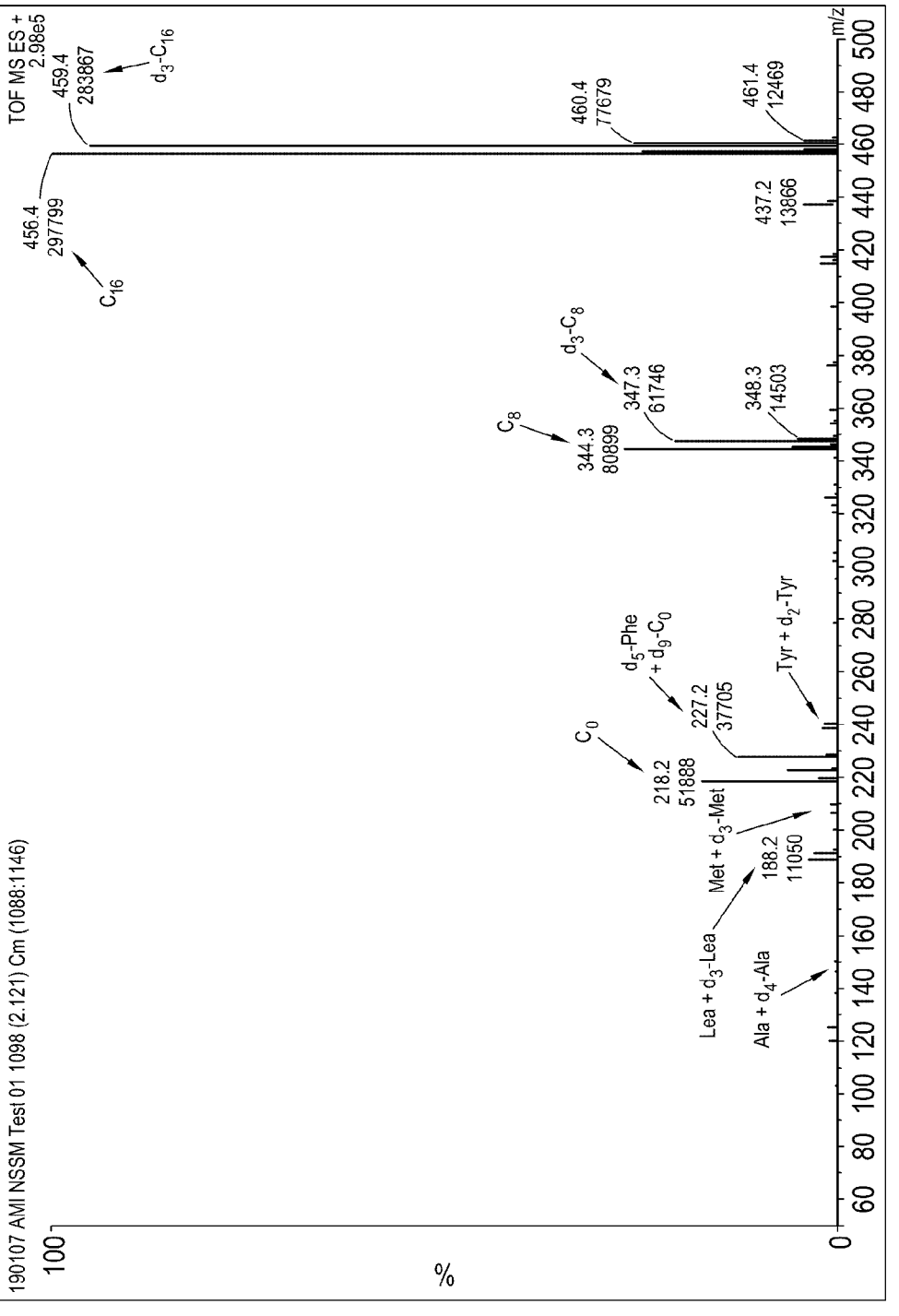
Figure 5:
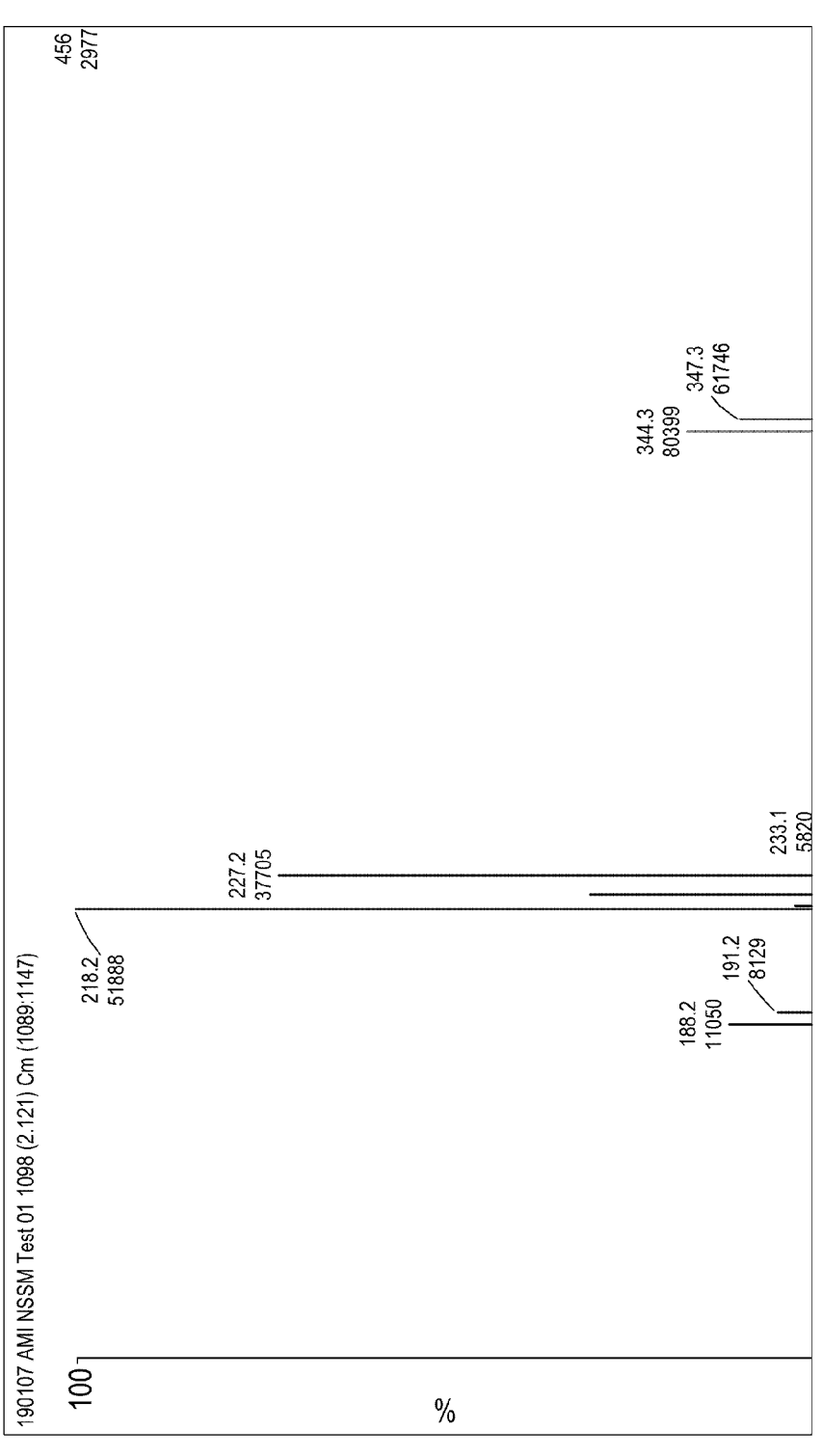
Figure 6:
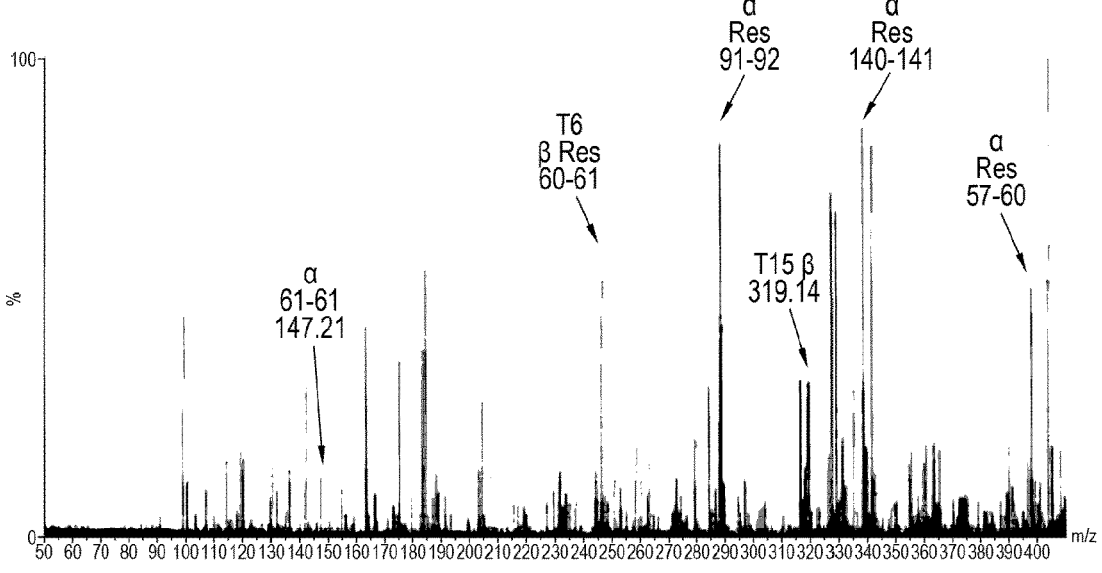
Figure 6:
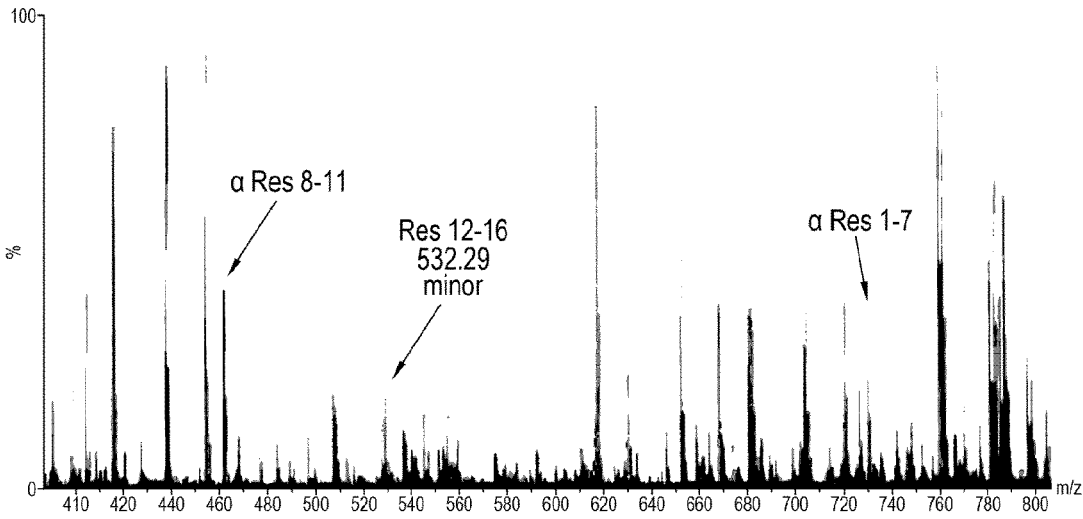
Figure 6:
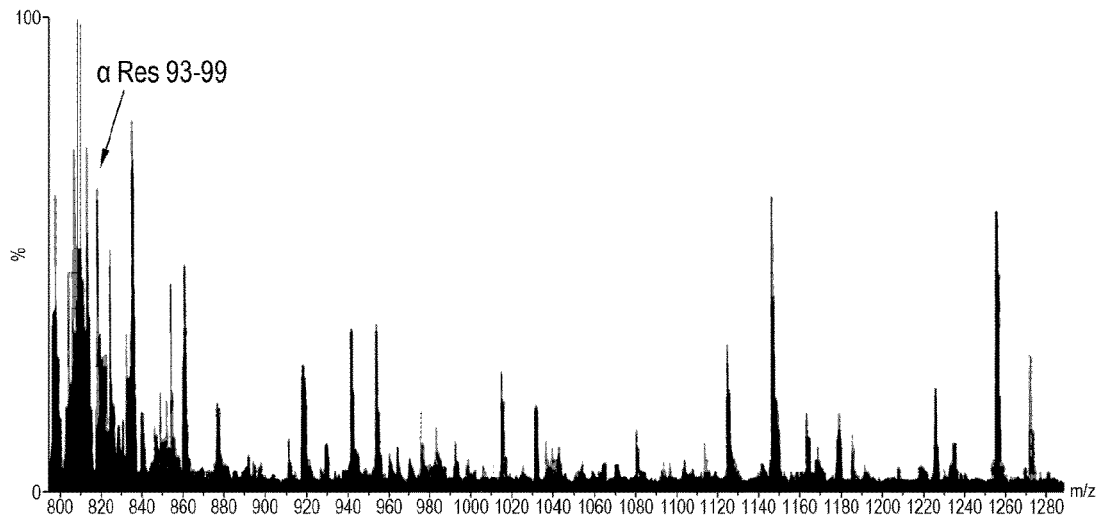

FIG. 3 illustrates a newborn screening ("NBS") workflow according to various embodiments and illustrates how a sample of dried blood from a card may be punched out into a sample well of a microtitre plate and then prepared for subsequent ionisation and transfer to the front end of a mass spectrometer by being ionised by an Acoustic Mist Ionisation ("AMI") ion source;

FIG. 4 shows experimental results obtained according to various embodiments and relates to an annotated Acoustic Mist Ionisation ("AMI") mass spectrum obtained from mass analysing a Neonatal Screening Sample Mixture ("NSSM") which comprises a reference sample of newborn screening ("NBS") metabolites;

FIG. 5 shows a magnified section of the Acoustic Mist Ionisation ("AMI") mass spectrum as shown in FIG. 4 and highlights a portion of the mass spectrum of interest; and FIG. 6 shows a mass spectrum obtained by mass analyzing a haemoglobin (Hb) digest using an Acoustic Mist Ionisation ("AMI") ion source according to various embodiments.

DETAILED DESCRIPTION

Various embodiments will now be described in more detail which relate to utilising an Acoustic Mist Ionisation ("AMI") ion source to ionise newborn, neonate or infant samples. In particular, various embodiments will be described in more detail which relate to improved methods of newborn, neonate or infant dried blood spot testing and for screening for metabolite disorders or inborn errors which may affect a newborn, neonate or infant.

According to other embodiments the sample may relate to a patient who may be a child or adult. For example, the method may be applied to screening children and adults for disorders such as PKU.

Furthermore, the method is not limited to screening for metabolite disorders but may also be applied to screening for endocrinology and hematology disorders.

As discussed above, the conventional approach to newborn screening (NBS) is to analyse a sample liquid which has been derived from a dried blood spot which has been processed by the addition of an extraction solvent. The sample liquid is then introduced into an Electrospray Ionisation ion source coupled to a liquid chromatography (LC) pump system. A number of inborn metabolic disorders can be screened for simultaneously but the process is relatively time consuming, potentially prone to sample carry-over and requires a relatively complex arrangement including an auto-sampler and a solvent pump system.

The present inventors have sought to overcome such problems and to provide a faster and improved method of newborn, neonate or infant screening (or child or adult screening) by utilising an Acoustic Mist Ionisation ion source to ionise a sample liquid derived from a dried blood spot from a newborn, neonate or infant (or child or adult).

Figure 1:
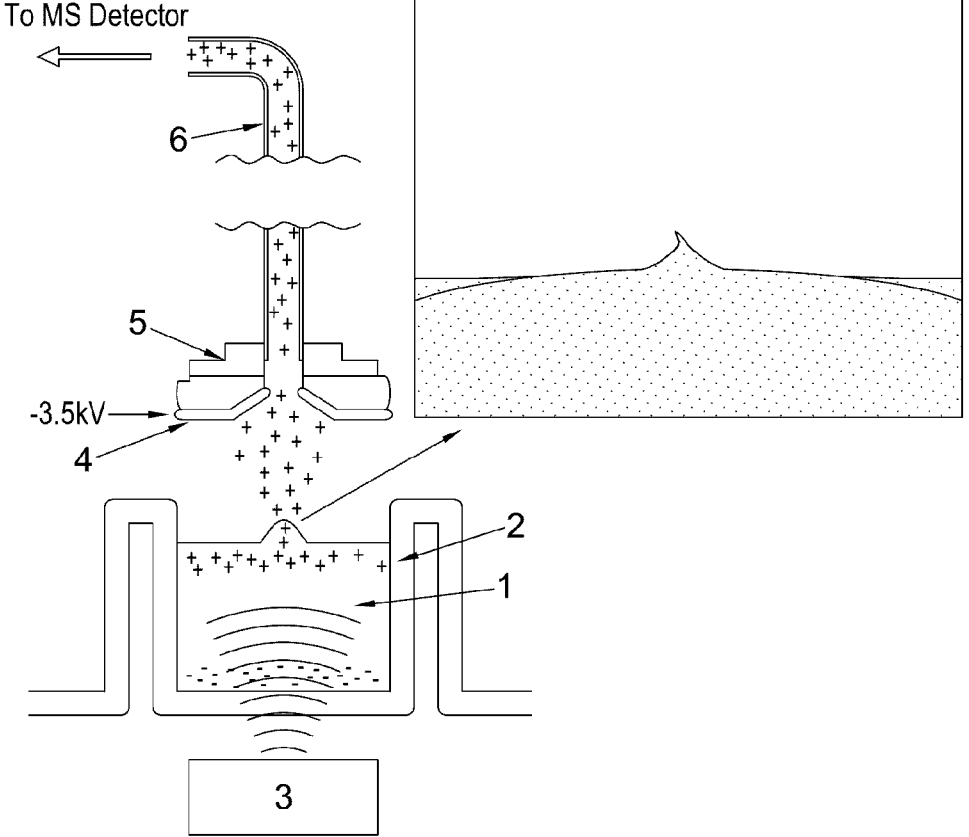
FIG. 1 illustrates various aspects of the process of acoustic mist ionisation which is utilised according to various embodiments to ionise a sample derived from a newborn, neonate or infant.

FIG. 1 illustrates some of the general principles of Acoustic Mist Ionisation which are utilised according to various embodiments. A liquid sample 1 to be analysed is obtained by extracting metabolites obtained from a dried blood spot derived from a human newborn infant (or other human patient) into a solvent solution. The liquid sample 1 to be analysed is shown provided in the sample well 2 of a sample plate.

The sample plate may comprise a microtitre plate. Microtitre plates are available in various formats. For example, according to an embodiment the sample plate may comprise a 96-well or 384-well microtitre plate or other sample plate.

An echo transducer or acoustic transducer assembly 3 is provided or otherwise located underneath or below the sample well 2 of the sample plate.

The ultrasonic transducer 3 which is located underneath the sample well 2 of the sample plate may be energised so as to cause ultrasonic acoustic waves or ultrasonic energy to be directed so as to pass through the base of the sample well 2 and into the sample 1 to be analysed. The sample plate and associated sample wells 2 may be acoustically transparent so as to permit the transfer the ultrasonic waves emitted from the ultrasonic transducer 3 into the sample liquid 1.

The ultrasonic transducer 3 may be arranged to emit ultrasonic waves having a frequency in the range: (i) 20-30 kHz; (ii) 30-40 kHz; (iii) 40-50 kHz; (iv) 50-60 kHz; (v) 60-70 kHz; (vi) 70-80 kHz; (vii) 80-90 kHz; (viii) 90-100 kHz; or (ix) >100 kHz.

The ultrasonic waves which are directed into the sample 1 in the sample well 2 result in a spray of droplets being ejected from the top or upper surface of the sample well 2. As will be discussed in more detail below, the spray of droplets which are ejected comprise charged droplets which form a mist of droplets.

As shown in FIG. 1, an electrically conductive collection nozzle or electrode 4 is located or otherwise provided above the sample 1 in the sample well 2. A relatively high voltage is applied to the collection nozzle or electrode 4 with the result that an electric field is maintained between the sample 1 and the collection nozzle or electrode 4. As a result, the spray of charged droplets is accelerated through the electric field towards the collection nozzle or electrode 4.

According to various embodiments the collection nozzle or electrode 4 may be held at a relatively high voltage (such as −3.5 kV) with the result that the application of such a relatively high voltage to the collection nozzle or electrode 4 and the resulting electric field which is generated causes charge separation within the liquid sample 1 contained within the sample well 2 of the sample plate or microtitre plate. Charged particles of opposite polarity to that of the collection nozzle or electrode 4 are drawn towards the surface of the sample 2 whereas charged particles of the same polarity to that of the collection nozzle or electrode 4 are repelled towards the bottom of the sample well 2. This charge separation effect is shown in FIG. 1.

The collection nozzle or electrode 4 may comprise an electrically conductive element such as a metal and may be mounted within a flexible insulator 5.

The sampling nozzle 4 may be maintained at the opposite polarity to the ionisation mode. For example, if it is desired to generate positively charged ions (in a positive ionisation mode) then the collection nozzle or electrode 4 may be maintained at a negative potential.

A transfer optic or transfer interface 6 having an opening may be secured within the flexible insulator 5 and may be arranged to receive charged droplets emitted from the sample 1 contained in the sample well 2 and which have been attracted towards the collection nozzle or electrode 4.

The image shown as an inset in FIG. 1 shows an image of a mound or cone of liquid being formed upon the surface of the liquid sample 1 and wherein a mist of fine droplets is ejected from the mound or cone in the general direction towards the collection nozzle or electrode 4.

The mist of charged droplets is attracted towards the collection nozzle or electrode 4 by the electric field and the charged droplets then pass into the transfer optic or transfer interface 6. The charged droplets are then onwardly transmitted to an atmospheric pressure interface of a mass spectrometer or to the initial stage of a mass spectrometer.

According to various embodiments the transfer optic or transfer interface 6 may be heated. For example, the transfer optic or transfer interface 6 may be heated to a temperature in the range 100-500° C., 150-400° C. or 200-300° C. According to various embodiments the transfer optic or transfer interface 6 may be heated to a temperature of approximately 250° C.

Figure 2:
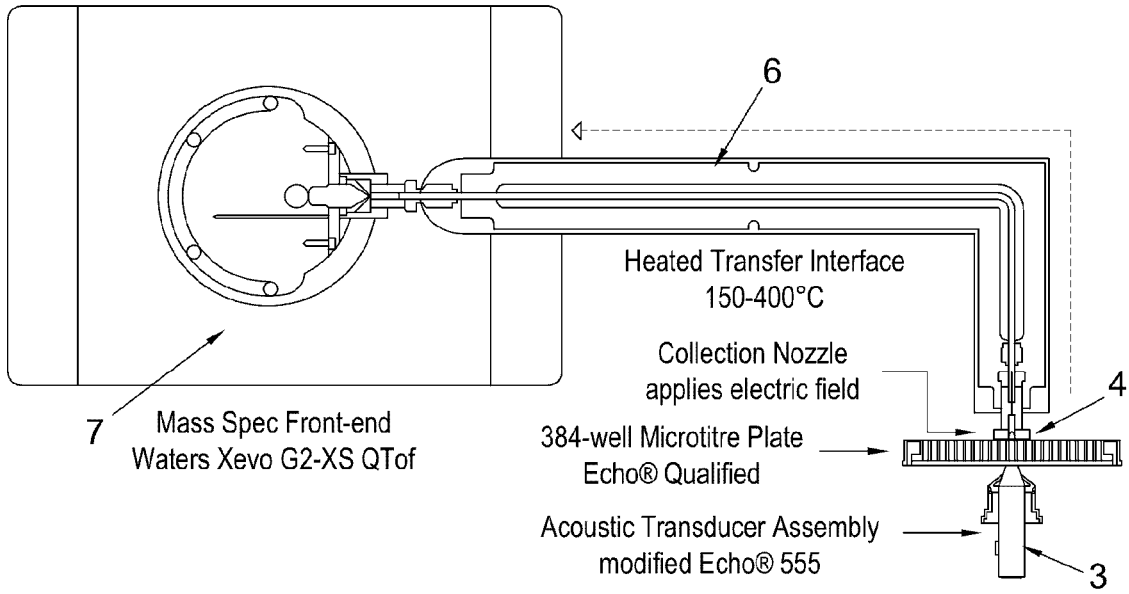
FIG. 2 shows in more detail an acoustic transducer assembly located underneath a 384-well microtitre plate according to various embodiments and illustrates how charged droplets relating to a newborn, neonate or infant sample may be emitted from the microtitre plate and are then transferred to the front end of a mass spectrometer via a heated transfer interface.

FIG. 2 shows in more detail how a heated transfer optic or transfer interface 6 may be used to transmit charged droplets emitted from the sample 1 in a sample well 2 of a sample plate towards the front end 7 or input stage of a mass spectrometer.

The mass spectrometer may, for example, comprise a WATERS® Xevo G2-XS QTof mass spectrometer.

Charged droplets which emerge from the heated transfer optic or transfer interface 6 may be arranged to pass through an atmospheric pressure interface into a vacuum chamber of the mass spectrometer. The charged droplets which are transferred into the mass spectrometer may be of a similar size to charged droplets produced by Electrospray Ionisation. The charged droplets or analyte ions may then be mass analysed by a mass analyser located within the mass spectrometer. The mass analyser may, for example, comprise a Time of Flight mass analyser.

The mass spectrometer may further comprise: (i) one or more ion guides; (ii) one or more ion mobility separation devices and/or one or more Field Asymmetric Ion Mobility Spectrometer devices; and/or (iii) one or more ion traps or one or more ion trapping regions.

Analyte ions transmitted into the mass spectrometer may be fragmented using a collision, fragmentation or reaction device located within a vacuum chamber of the mass spectrometer. The collision, fragmentation or reaction device may comprise any suitable collision, fragmentation or reaction device. For example, the collision, fragmentation or reaction device may be selected from the group consisting of: (i) a Collisional Induced Dissociation ("CID") fragmentation device; (ii) a Surface Induced Dissociation ("SID") fragmentation device; (iii) an Electron Transfer Dissociation ("ETD") fragmentation device; (iv) an Electron Capture Dissociation ("ECD") fragmentation device; (v) an Electron Collision or Impact Dissociation fragmentation device; (vi) a Photo Induced Dissociation ("PID") fragmentation device; (vii) a Laser Induced Dissociation fragmentation device; (viii) an infrared radiation induced dissociation device; (ix) an ultraviolet radiation induced dissociation device; (x) a nozzle-skimmer interface fragmentation device; (xi) an in-source fragmentation device; (xii) an in-source Collision Induced Dissociation fragmentation device; (xiii) a thermal or temperature source fragmentation device; (xiv) an electric field induced fragmentation device; (xv) a magnetic field induced fragmentation device; (xvi) an enzyme digestion or enzyme degradation fragmentation device; (xvii) an ion-ion reaction fragmentation device; (xviii) an ion-molecule reaction fragmentation device; (xix) an ion-atom reaction fragmentation device; (xx) an ion-metastable ion reaction fragmentation device; (xxi) an ion-metastable molecule reaction fragmentation device; (xxii) an ion-metastable atom reaction fragmentation device; (xxiii) an ion-ion reaction device for reacting ions to form adduct or product ions; (xxiv) an ion-molecule reaction device for reacting ions to form adduct or product ions; (xxv) an ion-atom reaction device for reacting ions to form adduct or product ions; (xxvi) an ion-metastable ion reaction device for reacting ions to form adduct or product ions; (xxvii) an ion-metastable molecule reaction device for reacting ions to form adduct or product ions; (xxviii) an ion-metastable atom reaction device for reacting ions to form adduct or product ions; or (xxix) an Electron Ionisation Dissociation ("EID") fragmentation device.

FIG. 3 shows in more detail a preferred workflow which relates to the steps of processing a dried blood spot ("DBS") obtained from a newborn, neonate or infant (or child or adult). A newborn, neonate or infant (or child or adult) may be subjected to a minor prick to cause a small drop of blood to form on the surface of the skin. The spot of blood may then be pressed onto a card or other substrate whereupon the blood spot will dry in a rapid manner to form a dried blood spot on the card. The card with the dried blood spot may then be processed. According to various embodiments the card and dried blood spot may be sent through the post (mail) to a screening laboratory for processing and analysis. Normally, the only requirement in respect of posting (mailing) a dried blood spot on a card is a requirement that the card is posted in a plastic envelope in order to prevent accidental wetting of the blood spot.

The various stages of extracting metabolites or analytes in solution from the dried blood spot on the card and providing a solution to be analysed into a sample well 2 of a sample plate are illustrated in FIG. 3.

At a first stage a 3 mm diameter sample from a dried blood spot (DBS) on a card or other substrate is punched 31 into a sample well of a (first) sample plate. It should be understood, however, that it is not essential that the size of the piece of dried blood spot which is punched out is 3 mm diameter. In particular, a larger or smaller diameter portion of dried blood spot may be punched out into the sample well of the sample plate. According to various embodiments the first sample plate may comprise a 96-well sample plate such as a microtitre plate.

At a subsequent stage 32, 100 μL (or another amount) of an extraction solvent may be added to the 3 mm diameter dried blood spot sample which has been punched out from the card.

Once an extraction solvent has been added to the section of the dried blood spot which has been punched out from the card, the sample plate may then be covered. The sample plate may then be shaken or otherwise agitated in a subsequent step 33. According to various embodiments the sample plate may be shaken or otherwise agitated for 30 minutes or a different length of time. Whilst the sample plate is being shaken or otherwise agitated the sample plate may be maintained at a desired temperature. For example, according to various embodiments the sample plate may be maintained at approximately body temperature (37° C.).

In a subsequent step 34, extract from the sample well of the first sample plate may be transferred to a sample well 2 of a second sample plate. The second sample plate may comprise an acoustic microtitre plate which is suitable for being loaded into an Acoustic Mist Ionisation system. The acoustic microtitre plate may, for example, comprise a 384-well plate and may be substantially transparent to ultrasonic waves. However, if the first sample plate comprises a 96-well sample plate then the second sample plate may also comprise a 96-well sample plate.

The second sample plate or acoustic microtitre plate may then be loaded at a subsequent stage 35 into an automated handling system.

The workflow and overall arrangement as shown in FIG. 3 is particularly beneficial when analysing newborn, neonate or infant samples as part of a process of newborn, neonate or infant dried blood spot screening. The workflow may also be used for child and adult screening.

In particular, the workflow shown in FIG. 3 according to various embodiments enables a high throughput to be achieved such that the throughput may be increased from about 30 tests/hour conventionally to as high as about 3,600 (or more) tests/hour. Accordingly, samples can be tested at a frequency of approximately 1 test/second.

It will be apparent, therefore, that a much higher throughput of newborn, neonate or infant samples (or child or adult samples) can be achieved which is not possible with conventional arrangements.

In certain circumstances it may be necessary or desirable to reanalyse a sample plate in a screening laboratory. The high level of throughput which can be achieved utilising an Acoustic Mist Ionisation ion source greatly facilitates the reanalysis of entire sample plates when needed with a minimal impact upon the high number of tests which can be achieved per hour.

Furthermore, using an Acoustic Mist Ionisation ion source to ionise the sample reduces the number and complexity of instrument platforms which would otherwise be needed for population-wide screening.

Using an Acoustic Mist Ionisation ion source to perform neo natal or other screening results in a reduction in system complexity. Since the Acoustic Mist Ionisation ion source comprises relatively few moving parts then the overall system has an improved robustness and there is a reduction in service requirements.

A reduction or elimination of carry-over is also achieved since the sample 1 does not come into physical contact with the autosampler or sampling devices. This is in contrast to conventional methods of newborn, neonate or infant screening which typically involve utilising a sampling needle which comes into direct contact with the liquid sample. The sample from a newborn, neonate or infant is then subjected to flow injection analysis using a tandem mass spectrometer ("FIA-MS/MS").

Another advantage of using an Acoustic Mist Ionisation ("AMI") ion source to ionise the sample 1 as opposed to using a conventional liquid chromatography pump system coupled to an Electrospray ionisation mass spectrometer (LC-ESI-MS) is that the use of a flow solvent is eliminated. The absence of any requirement to provide a flow of solvent greatly simplifies laboratory operations and eliminates the requirement to use a manufactured reagent kit.

Furthermore, conventional flow solvents typically comprise 80% aqueous acetonitrile which is both hazardous and expensive.

The pre-analytical laboratory workflow is also unaffected and sample preparation is similar to that used for FIA-MS/MS.

Acoustic Mist Ionisation ("AMI") when applied to newborn, neonate or infant screening (or child or adult screening) allows extremely rapid sampling times (up to three samples per second) to be obtained. Furthermore, the system is highly automated and involves automated handling of samples (from storage to delivery to the mass spectrometer). There is also no contact between the samples with the result that there is zero carry-over. A further benefit is that low sample consumption allows repeated sampling from the same well hundreds of times if needed.

FIG. 4 shows a mass spectrum relating to a Neonatal Screening Sample Mixture ("NSSM") which was ionised by an Acoustic Mist Ionisation source according to various embodiments.

The Neonatal Screening Sample Mixture comprised a solvent standard which was developed to determine the suitability of WATERS® FIA-MS/MS (flow injection analysis—tandem mass spectrometry) systems used for newborn, neonate or infant screening.

The solvent standard which was tested and subjected to Acoustic Mist Ionisation contained butyl esters of the following four amino acids and their respective internal standards: (i) alanine (Ala)/$d_4$-alanine; (ii) methionine (Met)/$d_3$-methionine; (iii) phenylalanine (Phe)/$d_5$-phenylalanine; and (iv) Tyrosine (Tyr)/$d_2$-tyrosine.

The solvent standard also contained the following three carnitine species: (i) free carnitine (C0)/$d_9$-C0; (ii) octanoylcarnitine (C8)/$d_3$-octanoylcarnitine; and (iii) palmitoylcarnitine (C16)/$d_3$-palmitoylcarnitine.

FIG. 4 shows ion peaks within the mass range 60-500 m/z which were identified as corresponding to constituents of the solvent standard. The observed mass to charge ratios (m/z) and associated relative intensities are consistent with corresponding mass spectra obtained using WATERS® FIA-MS/MS systems.

Accordingly, the experimental data shown in FIG. 4 demonstrates that an Acoustic Mist Ionisation ion source is highly effective at ionising a metabolite or analyte sample relating to a newborn, neonate or infant and illustrates how ion peaks and patterns of ion peaks which may be indicative of a disorder can be observed in the resulting mass spectra and mass spectral data.

FIG. 5 shows a magnified section of the Acoustic Mist Ionisation ("AMI") mass spectrum of the Neonatal Screening Sample Mixture ("NSSM") as shown in FIG. 4 and indicates how characteristic ion peaks which may be indicative of a newborn, neonate or infant disorder or inborn error can be readily identified from the mass spectral data.

Other embodiments are contemplated wherein haemoglobin from a newborn, neonate or infant may be tested or screened for disorders such as hemoglobinopathies. The method may also be used to screen for endocrinology disorders.

Accordingly, it should be understood that various embodiments are contemplated wherein the disclosed method may be used to screen for metabolite disorders and also for inborn errors such as inborn errors of endocrinology and hematology.

FIG. 6 shows a mass spectrum of a haemoglobin (Hb) digest obtained using an Acoustic Mist Ionisation ("AMI") ion source.

Various peaks of potential interest were identified and have been annotated in FIG. 6.

The experimental data shown in FIG. 6 is consistent with mass spectral data which is obtained conventionally, for example by analysing a blood sample using a flow-injection system coupled to an Electrospray Ionisation ion source and mass spectrometer.

According to various embodiments various hereditary or metabolic disorders and inborn errors may be detected by analysing mass spectral data obtained by ionising a blood sample utilising an Acoustic Mist Ionisation ion source including α-Thalassemia which is a common haemoglobin (Hb) disorder and which causes Hb H ($β_4$) disease.

Further embodiments are also contemplated. In particular, new extraction and reconstitution solvents may be developed that improve metabolite recovery from dried blood spots and/or which improve the reproducibility of the Acoustic Mist Ionisation process. For example, various tests have been performed analysing the performance of various modified extraction solvents, the minimum size of the dried blood spot which is required and the minimum volume of extraction solvent which needs to be added in order to achieve accurate and highly reproducible results.

Although the present invention has been described with reference to preferred embodiments, it will be understood by those skilled in the art that various changes in form and detail may be made without departing from the scope of the invention as set forth in the accompanying claims.

The invention claimed is:

1. A method of newborn screening ("NBS") comprising:
    preparing a metabolite or analyte sample for analysis by:
        punching, clipping or removing a portion of a dried blood spot ("DBS") relating to a newborn, neonate or infant and transferring the portion into a sample well of a first sample plate; adding an extraction sample or solvent to the DBS portion in the sample well of the first sample plate; shaking or agitating the dried blood spot portion and extraction sample or solvent in the sample well of the first sample plate; transferring an extract from the sample well of the first sample plate into a sample well of a second sample plate; and
    loading or positioning the second sample plate between an acoustic transducer assembly and a collection nozzle or electrode;
    directing ultrasonic energy or ultrasonic waves into the extract in the sample well of the second sample plate so as to cause a mist of charged sample droplets or sample ions to be ejected;
    mass analysing the charged sample droplets or sample ions; and
    determining whether or not one or more first metabolites or analytes indicative of a disorder or inborn error are present in the sample.

2. A method as claimed in claim 1, wherein the step of directing ultrasonic energy or ultrasonic waves into the extract comprises energising the acoustic transducer assembly.

3. A method as claimed in claim 1, wherein the step of directing ultrasonic energy or ultrasonic waves into the extract comprises energising an acoustic transducer assembly to emit ultrasonic waves having a frequency in a range: (i) 20-30 kHz; (ii) 30-40 kHz; (iii) 40-50 kHz; (iv) 50-60 kHz; (v) 60-70 kHz; (vi) 70-80 kHz; (vii) 80-90 kHz; or (viii) 90-100 kHz.

4. A method as claimed in claim 1, further comprising arranging the acoustic transducer assembly so that the acoustic transducer assembly does not directly contact extract.

5. A method as claimed in claim 1, further comprising applying an electric field between the collection nozzle or electrode and the sample well of the second sample plate in order to direct sample droplets into a transfer interface.

6. A method as claimed in claim 5, further comprising heating the transfer interface.

7. A method as claimed in claim 1, wherein the one or more first metabolites or analytes comprise free carnitine, acylcarnitines, amino acids, products of lysosomal enzymes or peptides.

8. A method of mass spectrometry comprising a method as claimed in claim 1.

9. A method as claimed in claim 5, further comprising heating the transfer interface to a temperature in the range 150-400° C.

10. A method as claimed in claim 5, further comprising heating the transfer interface to a temperature in the range 200-300° C.

11. A method as claimed in claim 1, wherein the first sample plate comprises a microtitre plate with a plurality of wells.

12. A method as claimed in claim 1, wherein the second sample plate comprises a microtitre plate with a plurality of wells.

13. A method as claimed in claim 1, wherein the second sample plate is transparent to ultrasonic waves.

14. A method as claimed in claim 1, wherein the first sample plate is maintained at a heated temperature while the first sample plate is being shaken or agitated.

15. A method as claimed in claim 14, wherein the first sample plate is maintained at about 37° C. while the first sample plate is being shaken or agitated.

16. A method as claimed in claim 1, wherein:

the second sample plate comprises a microtitre plate with a plurality of wells;

the second sample plate is transparent to ultrasonic waves; and the first sample plate is maintained at a heated temperature while the first sample plate is being shaken or agitated.

* * * * *